US012385820B2

(12) United States Patent
Ellson et al.

(10) Patent No.: US 12,385,820 B2
(45) Date of Patent: Aug. 12, 2025

(54) ACOUSTIC CONCENTRATION, TRANSFER AND ANALYSIS OF SAMPLES CONTAINING PARTICLES

(71) Applicant: Labcyte Inc., San Jose, CA (US)

(72) Inventors: Richard N. Ellson, Palo Alto, CA (US); Richard G. Stearns, Soquel, CA (US); Babur Hadimioglu, Mountain View, CA (US)

(73) Assignee: Labcyte Inc., San Jose, CA (US)

( * ) Notice: Subject to any disclaimer, the term of this patent is extended or adjusted under 35 U.S.C. 154(b) by 988 days.

(21) Appl. No.: 17/424,198

(22) PCT Filed: Jan. 31, 2020

(86) PCT No.: PCT/US2020/016259
§ 371 (c)(1),
(2) Date: Jul. 20, 2021

(87) PCT Pub. No.: WO2020/160501
PCT Pub. Date: Aug. 6, 2020

(65) Prior Publication Data
US 2022/0088617 A1    Mar. 24, 2022

Related U.S. Application Data

(60) Provisional application No. 62/800,304, filed on Feb. 1, 2019.

(51) Int. Cl.
*G01N 15/10* (2024.01)
*C12N 13/00* (2006.01)

(52) U.S. Cl.
CPC ............. *G01N 15/10* (2013.01); *C12N 13/00* (2013.01); *G01N 2015/1006* (2013.01)

(58) Field of Classification Search
None
See application file for complete search history.

(56) References Cited

U.S. PATENT DOCUMENTS

| | | | |
|---|---|---|---|
| 4,308,547 A | 12/1981 | Lovelady et al. | |
| 5,520,715 A | 5/1996 | Oeftering | |
| 6,029,896 A | 2/2000 | Self et al. | |
| 6,155,671 A | 12/2000 | Fukumoto et al. | |
| 6,416,164 B1 | 7/2002 | Stearns et al. | |
| 9,908,133 B2 | 3/2018 | Stearns et al. | |
| 10,112,212 B1 | 10/2018 | Stearns et al. | |
| 10,156,499 B1 | 12/2018 | Stearns | |
| 10,325,768 B1 | 6/2019 | Stearns | |
| 11,040,341 B2 | 6/2021 | Forbush | |
| 11,890,870 B2 | 2/2024 | Datwani et al. | |
| 2002/0094582 A1 | 7/2002 | Williams et al. | |
| 2003/0081040 A1 | 5/2003 | Therien et al. | |
| 2004/0056931 A1 | 3/2004 | Hadimioglu et al. | |
| 2004/0118953 A1 | 6/2004 | Elrod et al. | |
| 2005/0130257 A1 | 6/2005 | Mutz et al. | |
| 2005/0212869 A1 | 9/2005 | Ellson et al. | |
| 2006/0144871 A1 | 7/2006 | Van Tuyl et al. | |
| 2007/0057979 A1 | 3/2007 | Gardner et al. | |
| 2007/0153049 A1 | 7/2007 | Mutz et al. | |
| 2011/0121021 A1 | 5/2011 | Dudenhoefer et al. | |
| 2011/0134723 A1 | 6/2011 | Stearns et al. | |
| 2012/0006106 A1 | 1/2012 | Ellson et al. | |
| 2013/0235101 A1 | 9/2013 | Grace et al. | |
| 2013/0273591 A1 | 10/2013 | Attinger et al. | |
| 2016/0243569 A1 | 8/2016 | Stearns et al. | |
| 2017/0216856 A1 | 8/2017 | Stearns et al. | |
| 2018/0073029 A1 | 3/2018 | Hardee et al. | |
| 2018/0282781 A1 | 10/2018 | Mutz et al. | |
| 2018/0327618 A1 | 11/2018 | McManus | |
| 2019/0232275 A1 | 8/2019 | Forbush | |

FOREIGN PATENT DOCUMENTS

| | | |
|---|---|---|
| CN | 101954788 | 1/2011 |
| CN | 105842130 | 8/2016 |
| JP | 61272635 A | 12/1986 |
| JP | 0614956 U | 2/1994 |
| JP | 08290587 | 11/1996 |
| JP | 2004205510 A | 7/2004 |
| JP | 2004530863 A | 10/2004 |
| JP | 2018510360 A | 4/2018 |
| KR | 20100092378 | 8/2010 |
| WO | 2006105251 A2 | 10/2006 |
| WO | 2017017420 A1 | 2/2017 |
| WO | 2020160501 | 8/2020 |

OTHER PUBLICATIONS

U.S. Appl. No. 17/289,552 , "Notice of Allowance", Oct. 12, 2023, 8 pages.
CA3,117,800 , "Office Action", Jan. 8, 2024, 5 pages.
(Continued)

*Primary Examiner* — Teresa E Knight
(74) *Attorney, Agent, or Firm* — Kinney & Lange, P.A.

(57) ABSTRACT

Systems and methods described herein employ focused acoustic energy applied to a reservoir containing a fluid to eject a fluid sample from the fluid sample reservoir, e.g. to an inlet of an analytical device. In many embodiments, the ejected fluid sample traverses an air gap separating the inlet of the analytical device from an upper surface of the fluid in the fluid sample reservoir. In many embodiments, the ejected fluid sample comprises one or more droplets ejected from the fluid sample reservoir, which can contain particles suspended in the fluid sample.

13 Claims, 4 Drawing Sheets

(56) References Cited

OTHER PUBLICATIONS

JP2023-34446, "Office Action", Mar. 6, 2024, 1 page.
Application No. PCT/US2019/058620, International Preliminary Report on Patentability, Mailed on May 14, 2021, 7 pages.
Application No. PCT/US2019/058620, International Search Report and Written Opinion, Mailed on Feb. 5, 2020, 11 pages.
Application No. PCT/US2020/016259, International Preliminary Report on Patentability, Mailed on Aug. 12, 2021, 9 pages.
Tang et al., "On-Demand, Heatless Ejection of Sub-Mm-Sized Liquid Droplets", IEEE 30th International Conference on Micro Electro Mechanical Systems (MEMS), Jan. 22, 2017, pp. 1196-1199.
AU2019370221, "First Examination Report", May 5, 2022, 3 pages.
Application No. CA3,117,800, Office Action, Mailed on Feb. 28, 2022, 3 pages.
Application No. CN201980083114.8, Office Action, Mailed on Apr. 18, 2022, 22 pages.
IN202147020619, "First Examination Report", Oct. 2, 2021, 6 pages.
IN202147030408, "First Examination Report", Mar. 15, 2022, 8 pages.
AU2019370221, "Notice of Acceptance", Apr. 28, 2023, 3 pages.
AU2020215595, "Notice of Acceptance", May 2, 2023, 3 pages.
AU2020215595, "Third Examination Report", Feb. 28, 2023, 3 pages.
CN201980083114.8, Office Action, Mailed On Mar. 1, 2023, 8 pages.
AU2019370221, "Third Examination Report", Aug. 18, 2022, 2 pages.
AU2020215595, "First Examination Report", Aug. 5, 2022, 3 pages.
Application No. JP2021-544349, Office Action, Mailed on Jul. 29, 2022, 5 pages.
Application No. JP2021-548537, Office Action, Mailed on May 10, 2022, 11 pages.
"Effect of Process Characters of Nozzle-Free Ink-jet Forming on its Printed Body Properties", Journal of the Society of Powder Technology, vol. 46, 2009, pp. 13-19.
"Fundamentals of Rheology on Visco-Elastic Fluids", Journal of the Japan Society Material, vol. 84, No. 2, 2011, pp. 47-51.
AU2020215595, "Second Examination Report", Dec. 12, 2022, 2 pages.
CA3,117,800, Office Action, Mailed on Nov. 9, 2022, 3 pages.
CA3,127,492, Office Action, Mailed on Nov. 16, 2022, 4 pages.
JP2021-544349, Notice of Allowance, Mailed on Dec. 27, 2022, 3 pages.
JP2021-548537, Final Office Action, Mailed on Dec. 5, 2022, 11 pages.
SG11202107268W, Written Opinion, Mailed on Nov. 18, 2022, 5 pages.
U.S. Appl. No. 17/289,552, "Non-Final Office Action", Jul. 26, 2023, 13 pages.
CA3,117,800, "Office Action", Jul. 13, 2023, 3 pages.
CA3,127,492, "Notice of Allowance", Jul. 6, 2023, 1 page.
CN201980083114.8, "Notice of Decision to Grant", Jun. 20, 2023, 6 pages.
Gan et al., "Reduction of Droplet Volume by Controlling Actuating Waveforms in Inkjet Printing for Micro-pattern Formation", Journal of Micromechanics and Microengineering, vol. 19, Apr. 28, 2009, pp. 1-8.
Hadimioglu et al., "Moving Liquids With Sound, the Physics of Acoustic Droplet Ejection for Robust Laboratory Automation in Life Sciences", Journal of Laboratory Automation, vol. 21, No. 4, Feb. 2016, pp. 4-18.
KR10-2021-7013959, "Office Action", May 25, 2023, 8 pages.
"Acoustic Droplet Ejection", Available Online at: https://www.revolvy.com/main/index.phps=Acoustic+droplet+ejection, Publisher: Revolvy, Jun. 18, 2018, 1 page.
U.S. Appl. No. 10/821,311, "Final Office Action", Aug. 28, 2017, 7 pages.
U.S. Appl. No. 10/821,311, "Final Office Action", Sep. 25, 2014, 7 pages.
U.S. Appl. No. 10/821,311, "Non-Final Office Action", Dec. 18, 2015, 13 pages.
U.S. Appl. No. 10/821,311, "Non-Final Office Action", Oct. 18, 2016, 9 pages.
U.S. Appl. No. 10/821,311, "Notice of Allowance", Jun. 11, 2018, 10 Pages.
U.S. Appl. No. 14/041,156, "Final Office Action", Nov. 12, 2015, 8 pages.
U.S. Appl. No. 14/041,156, "Notice of Allowance", Aug. 1, 2018, 5 pages.
U.S. Appl. No. 15/256,417, "Non-Final Office Action", Jun. 28, 2018, 23 pages.
U.S. Appl. No. 15/256,417, "Notice of Allowance", Jan. 28, 2019, 5 pages.
U.S. Appl. No. 15/886,744, "Non-Final Office Action", Sep. 18, 2020, 7 pages.
U.S. Appl. No. 15/886,744, "Notice of Allowance", Feb. 23, 2021, 9 pages.
Hadimioglu et al., "Moving Liquids with Sound: The Physics of Acoustic Droplet Ejection for Robust Laboratory Automation in Life Sciences", Journal of Laboratory Automation, vol. 21, No. 1, 2016, pp. 4-18.
Luong et al., "Surface Acoustic Wave Driven Microfluidics—A Review", Bentham Science Publishers, Micro and Nanosystems, vol. 2, No. 3, Sep. 2010, 21 pages.
PCT/US2020/016259, "International Search Report and Written Opinion", Apr. 28, 2020, 10 pages.
Simon et al., "Ultrasonic Atomization of Liquids in Drop-Chain Acoustic Fountains", Journal of Fluid Mechanics, vol. 766, Mar. 2015, pp. 129-146.
SG11202107268W, "Notice of Decision to Grant", Aug. 25, 2023, 6 pages.

ACOUSTIC CONCENTRATION, TRANSFER AND ANALYSIS OF SAMPLES CONTAINING PARTICLES

CROSS-REFERENCE TO RELATED APPLICATIONS

This application is a U.S. national stage application of PCT/US2020/016259, filed Jan. 31, 2020, which claims the benefits of and priority to U.S. Provisional Patent Application No. 62/800,304, filed Feb. 1, 2019, the entire contents of both of which are incorporated herein by reference.

BACKGROUND

In life science research and clinical diagnostics, analytical detectors are often used to analyze the size of cells and/or particles disposed within a fluid sample. In view of increasing demand for analysis of the size of cells and/or particles disposed within a fluid, high-throughput approaches and related systems for analyzing the size of cells and/or particles are of interest. Analyzing particles within a fluid sample may require the sample to be loaded into a container and diluted to a particle density suitable for analysis or to have the bulk fluid properties be compatible with the counting and sizing method. Often, in particle sizing within fluid samples, the Coulter Principle is applied as it is effective for biological materials such as cells and viruses as well as non-conductive particles in general. For example, methods of utilizing the Coulter principle for particle counting are disclosed with reference to a Coulter counter (U.S. Pat. No. 2,656,508) to discriminate the presence of non-conducting cells or particles in a conductive fluid.

Coulter counting employs a conductive solution that forms a conductive path between electrodes where the presence or absence of non-conductive materials (e.g., non-conductive cells and/or particles) varies the resistance of the conductive path between the electrodes. If a particle is moving past the electrodes, the variation in the resistance can be used to determine the particle size. Commercial systems such as those from Beckman Coulter Inc. (Brea, California) can analyze conductive fluid samples by detecting changes in electrical impedance due to the presence of particles in the fluid as they pass through a measurement region positioned between two electrical terminals.

However, with Coulter counting, as with other methods of particle counting, sample transfer and sample dilution are potential sources of error or contamination. Therefore, improved methods of sample transfer and dilution of particle-containing samples are desired. Sample transfer methods using acoustic radiation (i.e., acoustic pressure waves) have been described in, e.g., U.S. Pat. No. 10,156,499. However, reliable transfer of particle-containing fluid for analysis of suspended particles has not previously been achieved.

BRIEF SUMMARY

Embodiments disclosed herein include a system having an acoustic radiation generator, a fluid sample reservoir containing a fluid sample, and an analytical instrument with an inlet that can receive fluid droplets. The fluid sample reservoir can be acoustically coupled with the acoustic radiation generator by an acoustic coupling medium, so that applied acoustic energy produced by the acoustic radiation generator can be transmitted through the fluid sample reservoir to interact with the fluid sample. Disclosed systems and methods employ an acoustic generator to apply a first tone burst of focused acoustic radiation to the fluid sample within the fluid sample reservoir to concentrate cells or particles within the fluid sample, and to subsequently apply a second tone burst of focused acoustic radiation by the acoustic radiation generator to the fluid sample at a location corresponding to the concentrated cells or particles, in order to eject a droplet from the reservoir containing at least one cell or particle. A droplet can be ejected to an inlet of an analytical instrument such as, e.g., a cell or particle counter or any other suitable instrument, or can be transferred for any other suitable purpose such as, e.g., culture splitting, slide loading for microscopy, dilution, and the like.

DETAILED DESCRIPTION

Various embodiments of the present disclosure include acoustic systems and methods for transferring particle-containing fluid from a sample reservoir to a target, such as but not limited to a sample container, fluid well plate, sample medium, or analytical device inlet. For example, the transfer of a fluid sample from a sample reservoir to an analytical detector can be achieved via the application of focused acoustic radiation to fluid within the sample reservoir. The sample reservoir can be positioned to place a fluid surface of the fluid in alignment with an inlet of an analytical device and separated from the inlet by a suitable gap.

Focused acoustic radiation, emitted in patterns referred to herein as tone bursts, can then be applied to the fluid in the sample reservoir to eject the fluid sample from the sample reservoir so that the ejected fluid sample traverses the gap and enters the inlet of the analytical detector. Many fluid samples are suitable for acoustic transfer, including but not limited to most aqueous solutions. For example, the fluid sample can include a volume of electrolytic liquid with one or more cells and/or particles suspended within the volume of electrolytic liquid.

In some embodiments, cells and/or particles suspended within the fluid sample are concentrated near the upper fluid surface, prior to the ejection of the fluid sample, via the application of focused acoustic radiation to the fluid in the sample reservoir. By first concentrating the particles and/or cells near the upper fluid surface, the concentration of the particles and/or cells within the ejected fluid sample can be increased relative to the average concentration of the particles and/or cells within the sample reservoir. The acoustic approach contrasts with existing approaches for sample handling vis-a-vis loading samples for analysis by analytical devices, in which typical sample reservoirs are placed in fluid communication with an inlet of the analytical device to provide a fluid communication path by which the fluid sample is transferred to the analytical device from the sample reservoir.

The sample reservoir can positioned relative to the inlet of the analytical device without necessitating direct contact with the inlet of the analytical device, thereby enabling successive and rapid transfer of fluid samples from multiple reservoirs to the same analytical device, increasing throughput and efficiency, reducing or preventing cross-contamination, and improving sample consistency. Additionally, the ability to concentrate the cells and/or particles in the ejected fluid sample enables the use of the systems and approaches described herein in the purification of fluids.

In many embodiments, devices and methods described herein employ focused acoustic energy applied to a reservoir containing a fluid to eject a fluid sample from the fluid sample reservoir to an inlet of an analytical device. In many embodiments, the ejected fluid sample traverses an air gap separating the inlet of the analytical device from an upper surface of the fluid in the fluid sample reservoir. In many embodiments, the ejected fluid sample comprises one or more droplets ejected from the fluid sample reservoir.

Any suitable analytical device can be employed. For example, in some embodiments, the analytical device is adapted to measure the number and size of the particles contained within the transferred fluid sample. For example, the detector could use an electrical impedance meter as in a Coulter counter (U.S. Pat. No. 2,656,508) to discriminate the presence of non-conducting cells or particles in a conductive fluid. As additional examples, the detector could be optical and measuring scattered light as in hematology analyzers.

The devices and methods describe herein can be used to provide high-throughput analysis of fluid samples from multiple fluid sample reservoirs by a single analytical detector. For example, the devices and methods described herein can be used to transfer a first fluid sample (e.g., a conductive fluid containing at least one non-conductive particle) from a first reservoir to the inlet aperture of a detector, to analyze the first fluid sample (e.g., measure to number and size of the particles within the first fluid sample), and then to rapidly switch to the application of focused acoustic energy to a second reservoir to transfer a second fluid sample to the inlet of the detector.

The devices and methods describe herein can be used to increase the concentration of cells and/or particles within the ejected fluid sample. For example, in some embodiments, focused acoustical radiation is applied to the fluid sample reservoir, prior to the ejection of a fluid sample, to concentrate cells and/or particles near the upper surface of the fluid within the fluid sample reservoir. Such pre-ejection concentration can be used for any suitable purpose. For example, to reduce the total volume of fluid transferred by focused acoustic energy from a sample reservoir to the inlet of the analytical device, focused acoustic energy can be applied to concentrate the particles in a nodal focus region formed near the upper surface of the fluid and then an acoustic energy pulse can be applied to the fluid in the sample reservoir to eject the fluid near the nodal focus point as a fluid droplet wherein the particle density of the droplet exceeds the average particle density within the fluid outside the nodal focus point.

In contrast, focused acoustic ejection of droplets in rapid succession from a reservoir to the measurement aperture can provide fluid coverage of the aperture only. This precludes the need for a larger quantity of fluid to be in contact with the aperture to provide immersion. Drawing of the fluid through the aperture to perform the measurement can also clear the face of the measurement aperture and prepare the measurement system to receive another sample. The completion of the first sample measurement can occur after a pre-determined volume is transferred to the measurement aperture face or, optionally, based on an analysis by the measurement systems of the particles detected. The analysis could include, but is not limited to the total number of particles or number of particles within a given size range.

Once the completion criteria is met (i.e., number of droplets of sample transferred or some other analysis criteria), the transfer of droplets from the reservoir is terminated. The device can then be configured to transfer from the next reservoir. The next reservoir could be another container capable of supporting focused acoustic ejection, including a separable container such as a micro tube or a connected on such as a well in a multi-well plate (such as 384-well or 1536-well microplates, other suitable microplates, or other suitable containers).

Prior to the acoustic transfer of droplets from the next sample reservoir, the state of the measurement aperture can be determined to see if the previous sample has been drawn into the interior of the measurement device. This could be done by a variety of means such as optical through a camera or, preferably, through the signal provided by the measurement aperture itself as the gas atmosphere in the vicinity of the aperture is drawn into the orifice. The presence of a non-conductive gas at the orifice would be easily distinguished from the presence of non-conductive particles in the conductive fluid due to the much larger reduction in current. The Coulter method generally limits the size of particles for measurement to be under 60% of the diameter of the aperture size to maintain fidelity of measurement in contrast the gas being drawn into the aperture would span the entire aperture.

In some embodiments of the invention, this drop in conductivity due to the ingestion of air into the measurement aperture could be coupled to the control of the flow rate of the pumping system pulling fluid from the interior region (behind the measurement aperture). For example, when the current flow at the aperture was reduced to a level below that generated by the largest particle and consistent with air ingestion across the entire aperture, the pump could be shut off as all the sample containing fluid had passed through the orifice. Further, an optional ready signal could be sent to the acoustic drop generator to indicate that the measurement aperture was in a state suitable to receive a sample from the next reservoir without risk of contamination.

As the measurement aperture face will be repeatedly wetted and de-wetted as fluid samples are transferred from reservoirs and then drawn into the measurement aperture, it would be desirable for the measurement aperture face to be comprised or coated with a chemically inert, resistant, and/or non-wetting material that will not retain either the particles or the electrolyte fluid. For example, according to some embodiments, the inlet of the analytical instrument can include a hydrophobic coating, or can be formed from a hydrophobic material, that will cause droplets on the inlet of the analytical instrument to remain coherent until they have been pulled through the inlet without leaving residue or splitting into multiple droplets on the surface of the inlet.

"Low-throughput" methods for loading particle analysis instruments combine immersion of measurement aperture in large sample volumes aspiration and frequently lack automated sample changing mechanisms. Even with automation, such methods are limited in speed due to the constraints of longer movements of from one immersive state to the next.

Figure 1A:
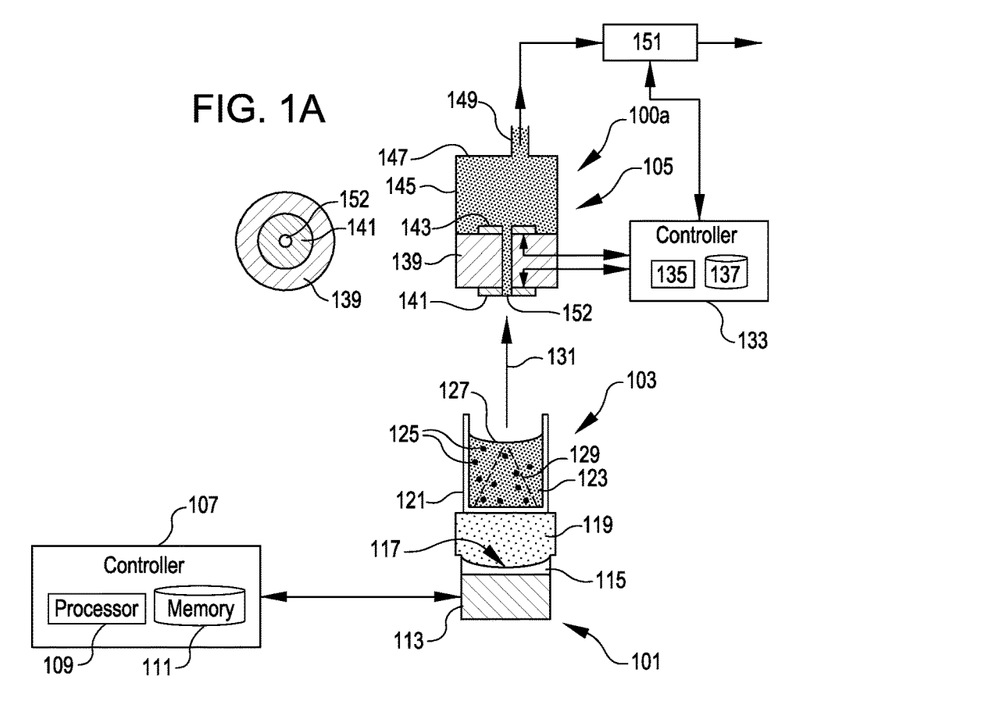
FIG. 1A is a simplified schematic diagram of a fluid analysis system, in accordance with various embodiments of the present disclosure.

Turning now to the drawings, FIG. 1A is a simplified schematic diagram of a fluid sample analysis assembly that includes an acoustic ejector assembly 101, a fluid sample reservoir 103, and an analytical device assembly 105. The ejector assembly 101 can include a focused acoustic radiation generator 113 and a focusing element 115 such as, but not limited to, a concave, diffractive, or annular surface coupled with the acoustic radiation generator 113 and shaped to focus acoustic energy from a focusing element surface 117. The ejector assembly 101 can be acoustically coupled with the fluid sample reservoir 103 by way of an acoustic coupling medium 119, whereby patterns of acoustic pressure generated by the ejector assembly 101 travel through the acoustic coupling medium into the fluid sample reservoir 103.

The fluid sample reservoir 103 can include a reservoir body 121 such as, but not limited to, a standalone fluid well or fluid-containing tube, a well in a well plate, or any other suitable fluid container. The fluid sample reservoir 103 can be at least partly filled with a fluid sample 123, optionally containing suspended particles 125. Particles 125 can include, e.g., nanoparticles or microparticles, cells, macromolecules, or other suitable particles, as well as mixtures including two or more of the aforementioned particle types as individual particles or any of the aforementioned particle types bound together.

The fluid sample 123 extends to a fluid surface 127 in the fluid sample reservoir 103, which is positioned in alignment with, and at an appropriate distance, for fluid transfer from the fluid sample 123 to the analytical device assembly 105. The analytical device assembly 105 is positioned to receive a fluid sample ejected from the fluid sample reservoir 103 via the application of focused acoustic radiation applied to the fluid sample by the acoustic radiation generator 113 and focused by the focusing element 115, in accordance with embodiments. FIG. 1A depicts the acoustic radiation generator 113 with focusing element 115 coupled to the fluid sample reservoir 103, with suspended particles 125 in the fluid sample reservoir.

Under the control of a controller 107, which can include a computer system including one or more processors 109 and non-transitory memory 111, the acoustic radiation generator 113 can be activated to produce acoustic radiation in any number of tone bursts at a wide range of frequencies and/or patterns, the tone burst parameters dictating the effect of the tone bursts on the fluid sample 123. For example, a first tone burst pattern at a first amplitude can be used for effecting movement of the particles 125 within the fluid sample 123 without ejecting droplets, e.g., to concentrate particles at the fluid surface 127 within a cone-shaped acoustic beam 129 characterizing the tone burst. A second tone burst pattern, different from the first, at a second amplitude, can be used for producing droplets that will separate from the fluid sample 123 at the fluid surface 127, carrying particles 125 therewith.

The analytical device assembly 105 can include a variety of specific analytical devices or detectors, including but not limited to a particle counter. As shown in FIG. 1A, the analytical device assembly 105 can include, e.g., an aperture 152 of a detector 139 of the analytical device having electrodes 141, 143 positioned across the aperture for inducing a voltage over a length of the aperture and detecting variations in conductivity over the same length from the first electrode 141 positioned outside the detector 139 to the second electrode 143 positioned adjacent a collection chamber 145. In operation, a controller 133, also including a processor 135 and memory device 137, can induce the voltage difference across the electrodes 141, 143 and can thereby measure conductivity through the aperture, with variations in conductivity indicative of the presence or absence of particles and, in some cases, indicative of the size of the particles. Collected fluid 147 within the collection chamber 145 can be removed at a predetermined rate by way of a pump 151, which may also be under the control of controller 133. The acoustic ejector assembly 101 and the analytical device assembly 105 can be controlled by the same control system and concomitant controllers, or can be controlled by separate controllers.

Figure 1B:
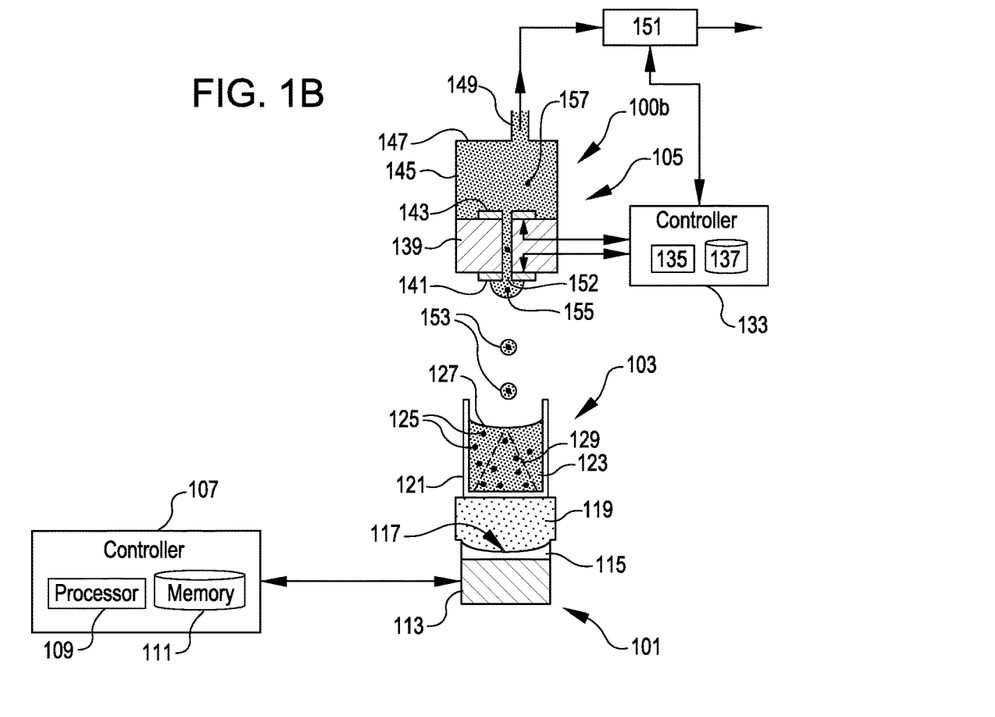
FIG. 1B is a simplified schematic diagram of the fluid sample analysis system of FIG. 1A depicting droplets of a fluid sample ejected from a fluid sample reservoir to an inlet of an analytical device via application of focused acoustic radiation.

In use, the acoustic ejector assembly 101 can be operated by the controller 107 to eject droplets from the fluid sample reservoir 103 for analysis by the analytical device assembly 105, as illustrated in FIG. 1B. FIG. 1B is a simplified schematic diagram of the fluid sample assembly of FIG. 1A depicting droplets 153 of a fluid sample 123 ejected from the fluid sample reservoir 103 to an inlet of the aperture 152 of the analytical device assembly 105 via application of focused acoustic radiation by the focused acoustic radiation generator 113. As droplets 153 are ejected from the fluid surface 127 of the fluid sample 123, the droplets may cross an air gap between the fluid sample reservoir 103 and the analytical device assembly 105 before deposition at an inlet of the aperture 152 on the detector 139. According to various embodiments, a single droplet containing particles may be sufficient for analysis, or an accumulation 155 of sample fluid from multiple droplets may be collected for obtaining a desired volume of fluid sample 123. When one or more droplets 153 have been collected on an outer surface of the detector 139 at the inlet of the aperture 152, a pump 151 can be activated to pull the accumulation 155 of sample fluid through the aperture 152 in order to obtain a particle count or to analyze attributes of the obtained particles, e.g., by measuring electrical impedance within a measurement region of the aperture 152 as the electrical impedance is altered by the presence of particles.

Figure 1C:
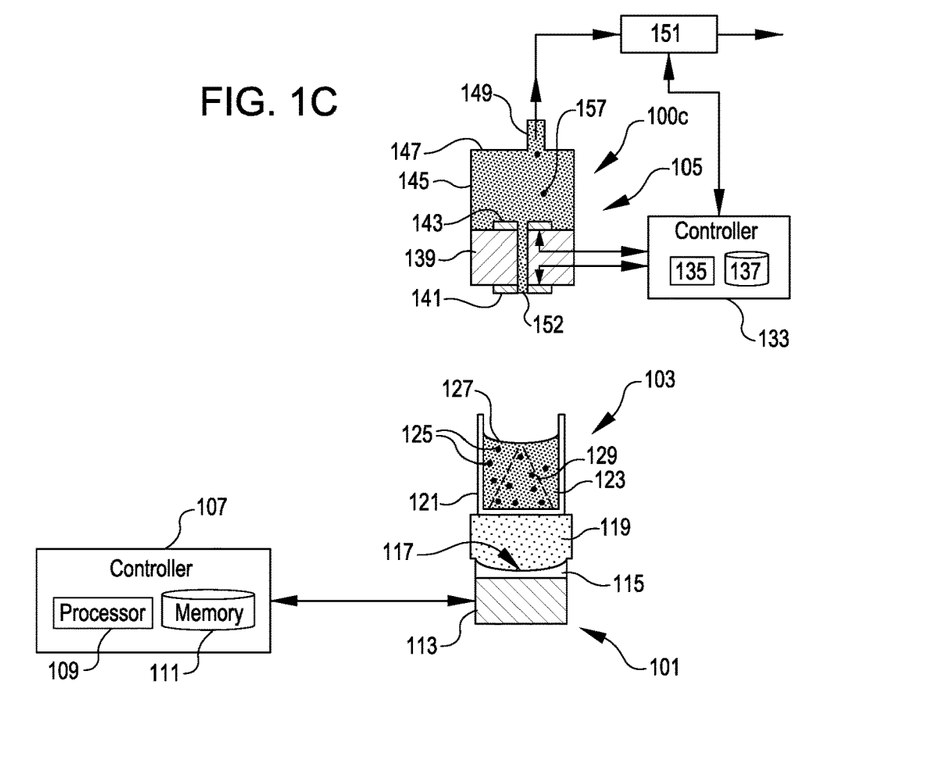
FIG. 1C is a simplified schematic diagram of the fluid sample assembly of FIG. 1A following completion of the ejection of the fluid sample from the fluid sample reservoir to the analytical device.

FIG. 1C is a simplified schematic diagram of the fluid sample assembly of FIG. 1A following completion of the ejection of the fluid sample 123 from the fluid sample reservoir 103 to the analytical device assembly 105. In FIG. 1C, no droplets are being ejected from the fluid sample reservoir 103, and the micro pump 151 has carried the meniscus of the fluid accumulation 155 of conductive sample fluid from the surface of the outer electrode 141 inside a measurement region of the aperture 152, and thus broken electrical contact between the inner and outer electrodes 141, 143, at which time the controller 133 can signal the pump 151 to cease the evacuation of the collection chamber. Conversely, the formation of a new accumulation 155 of sample fluid on the outer electrode 141 cause electrical contact between the inner and outer electrodes 141, 143. When electrical contact is reestablished, the conductivity can be detected by the controller 133 and signal that the pump 151 can be reactivated.

The analytical processes described above can be repeated for sequentially ejected samples of particle-containing fluid from the same reservoir or from different reservoirs, which can be moved into place and aligned with the acoustic ejector assembly 101 and the analytical device assembly 105 to facilitate droplet ejection and analysis. Typically, aligning a new reservoir involves at least orienting the reservoir in two dimensions so that an ejected droplet traverses an air gap between the fluid surface 127 and the inlet of the aperture 152. In some embodiments, the vertical distance of the fluid reservoir assembly 103 can be adjusted as well, in order to align the upper fluid surface 127 of the fluid sample 123 with a focus of the acoustic beam generated by the acoustic radiation generator 113 and focused by the focusing element 115. According to some embodiments, multiple and potentially many fluid sample reservoirs 103 can be rapidly positioned, sampled, and repositioned to allow for rapid analysis of particle-containing fluid from many fluid reservoirs. Multiple fluid reservoirs can be separate containers, which may be positioned on a movable stage or other actuator individually; or can be wells on a multi-well plate or microplate.

Figure 2:
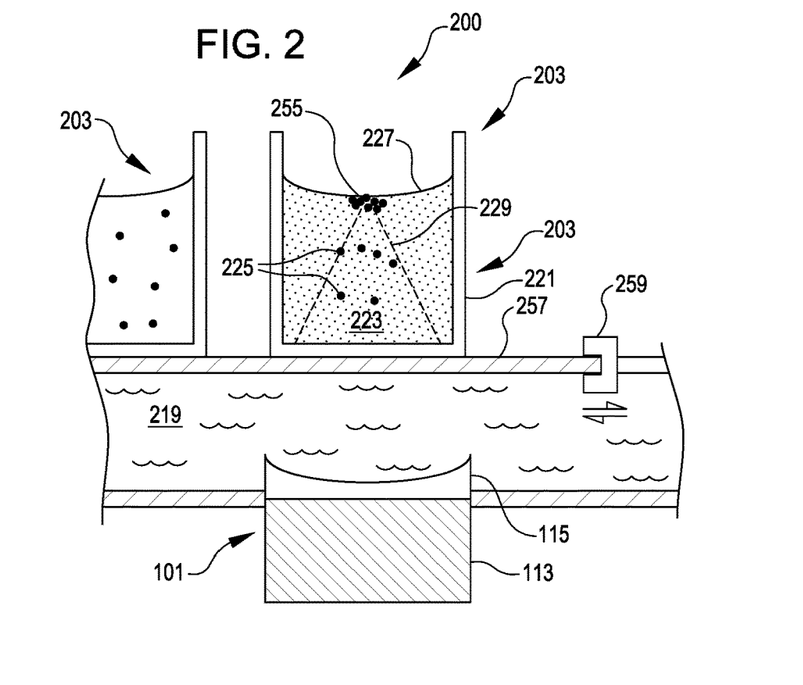
FIG. 2 depicts concentration of cells and/or particles at the upper fluid surface of the fluid sample reservoir via application of focused acoustic radiation prior to ejection of a fluid sample having increased concentration of cells and/or particles from the fluid sample reservoir.

FIG. 2 illustrates a sample reservoir assembly 200 that depicts concentration of cells 225 and/or particles at the upper fluid surface 227 of a fluid sample reservoir via application of focused acoustic radiation prior to ejection of a fluid sample having increased concentration of cells and/or particles from the fluid sample reservoir. The sample reservoir assembly 200 includes at least one fluid sample reservoir 203, similar to fluid sample reservoir 103 (FIGS. 1A-1C), which can be positioned on or connected with a stage 257 along with one or more other sample reservoirs, An acoustic ejector assembly 101 that includes an acoustic radiation generator 113 coupled with a focusing element 115 can be acoustically coupled with the fluid sample reservoir 203 by an acoustic coupling medium 219. In use, the acoustic ejector assembly 101 can generate a focused acoustic beam 229 to create a nodal concentration 255 of particles or cells 225 near the upper fluid surface 227 of the fluid sample 223. Acoustic generated drops produced from the fluid sample reservoir 203, when the particles are acoustically concentrated, will have higher concentrations of particles than bulk fluid and reflect particle density in focal region near surface. Methods for how to adjust the frequency and therefor change the wavelength of the acoustic radiation within the sample fluid are known to those of skill in the art. Selecting the number of nodal and anti-nodal planes for efficient particle trapping would depend on many factors including density, particle size, particle stiffness and the like. Dynamic measurement of fluid thickness through sonar-type methods may be required to maintain nodal states, and may also require changing the number of nodal planes as reservoir fluid depth changes. Such methods for measurement are known to those of skill in the art. Sensing the resonant state can also be detected according to methods described in, e.g., Hueter, Theodor F., and Richard H. Bolt. Sonics: techniques for the use of sound and ultrasound in engineering and science. New York: Wiley, 1955.

Figure 3A:
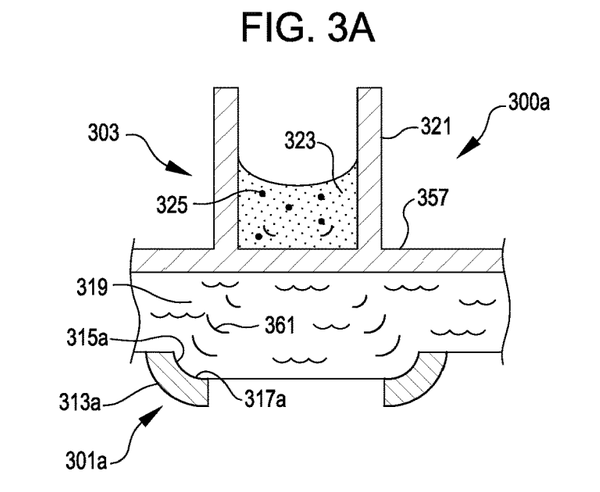
FIG. 3A, FIG. 3B, and FIG. 3C are simplified schematic diagrams showing embodiments of focused acoustic radiation generators coupled to a respective fluid sample reservoir, in accordance with embodiments.
Figure 3B:
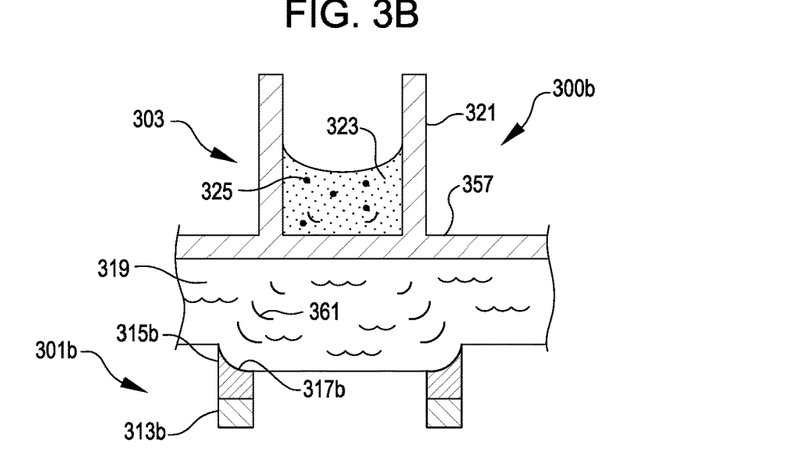
Figure 3C:
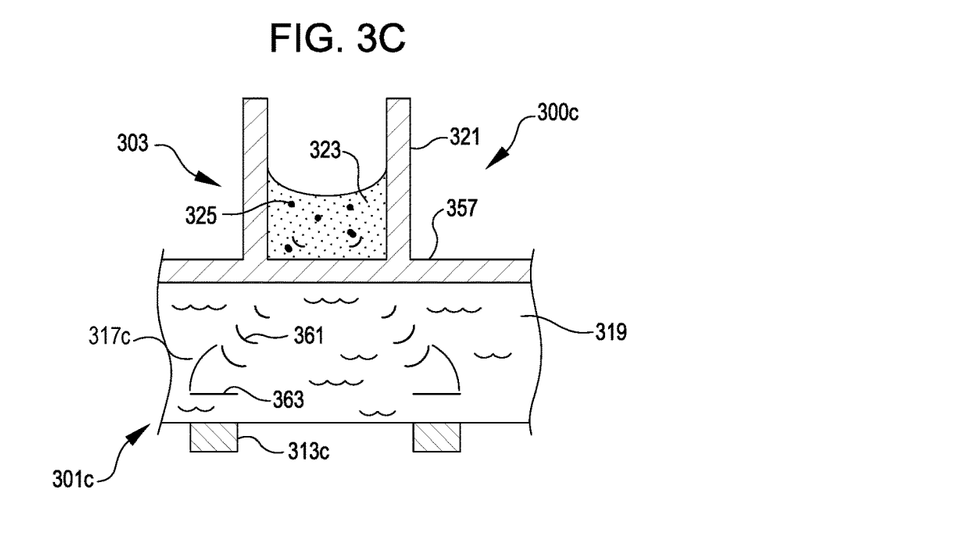

FIG. 3A through FIG. 3C are simplified schematic cross-section diagrams showing embodiments of focused acoustic radiation generators coupled to a respective fluid sample reservoir, in accordance with embodiments. These configurations of acoustic radiation generators are configured to generate patterns of acoustic radiation suitable for guiding suspended particles towards a target volume in order to concentrate particles near an upper surface of the fluid sample reservoir in order to facilitate droplet ejections containing particles. Note that at least one acoustic generator and focusing element (or lens) in each of FIG. 3A through FIG. 3C is annular. These acoustic generators and/or focusing elements can include a concave, focusing piezoelectric element, a reflective or refractive lens element, or a phased-array configuration (not shown), or other suitable acoustical wave focusing element. The shape of the focusing beams in these configurations are primarily controlled by the shape of the lens element, or in the case of a phased-array transducer, on the amplitude and phase of the drive signals provided to the acoustic radiation generator(s). It should be noted that the shape of the focusing beam is optimized to achieve maximum efficiency of guiding the particles to the target zone. These beam shapes include spherically converging beams, Gaussian beams, and Bessel beams, as well as other suitable beam shapes, e.g., as described in Fan, Xudong and Zhang, Likun, Simultaneous trapping and pulling by acoustical Bessel beams as stable tractor beams, The Journal of the Acoustical Society of America 145, 1817 (2019).

Each of FIGS. 3A-3C illustrate a fluid sample reservoir 303 containing a fluid sample 323 with suspended particles 324. A reservoir body 321 of the fluid sample reservoir may extend away from a stage or plate 357 on which the fluid sample reservoir 303 rests or to which the fluid sample reservoir can be attached. Alternatively, the fluid sample reservoir 303 can be positioned without a sample stage or plate. The fluid sample reservoir 303 can be acoustically coupled with an acoustic ejector 301 by way of an acoustic coupling medium 319. Preferably, this medium is contained to allow for free movement of the fluid sample reservoir 303 with respect to the acoustic ejector 301.

In FIG. 3A, a first example arrangement 300*a* includes an annular acoustic ejector 301*a* formed by a combined acoustic radiation generator 313*a* and focusing element 315*a*, whereby the acoustic radiation generator is shaped having a concave working face 317*a* that directs acoustic waves 361 into the coupling medium 319 in a conical shape such that, when the acoustic waves 361 interact with particles 325 in the fluid sample 323, the acoustic waves tend to concentrate the particles at a focal region or node. Fluid sample reservoir 303 can be positioned with respect to the acoustic ejector 301*a* to place the focal region at any suitable location in the fluid sample reservoir 303, typically near an upper surface.

In FIG. 3B, a second example arrangement 300*b* includes an annular acoustic ejector 301*b* formed by a planar and annular acoustic radiation generator 313*b*, coupled with an annular and curved focusing element 315*b*, whereby the focusing element has a concave working face 317*b* that directs acoustic waves 361 into the coupling medium 319, according to a similar conical pattern as the waves produced according to arrangement 300*a*.

FIG. 3C, illustrates a third example arrangement 300*c*, in which an annular acoustic ejector 301*c* formed by an annular acoustic radiation generator 313*c* that transmits acoustic waves into the coupling medium 319, where curved focusing elements 317*c* redirects the acoustic waves in order to achieve a similar conical pattern as the waves produced according to arrangements 300*a* or 300*b*.

The transducers of FIG. 3 are designed to operate at frequencies where the generated acoustic waves would have a high efficiency of guiding the particles, within the size limits of interest, towards the target focal zone with high efficiency. The driving signals are optimized to produce a high level of efficacy as well. The waveforms would include a continuous waveform (CW) or a long tone-burst at the desired frequency to produce a standing acoustic wave pattern to trap the particles in the resonant or anti-resonant nodes of the acoustical field. If desired, the drive frequency can be swept slowly to provide a means to move them towards the target zone. It is also possible to use an acoustic waveform that will create an acoustic streaming effect to stir, mix, and help guide the particles towards the target zone. It is also understood that the above drive mechanisms (particle trapping and streaming) to produce the desired effects can be combined to produce the ultimate efficiency of guiding the particles.

Figure 4:
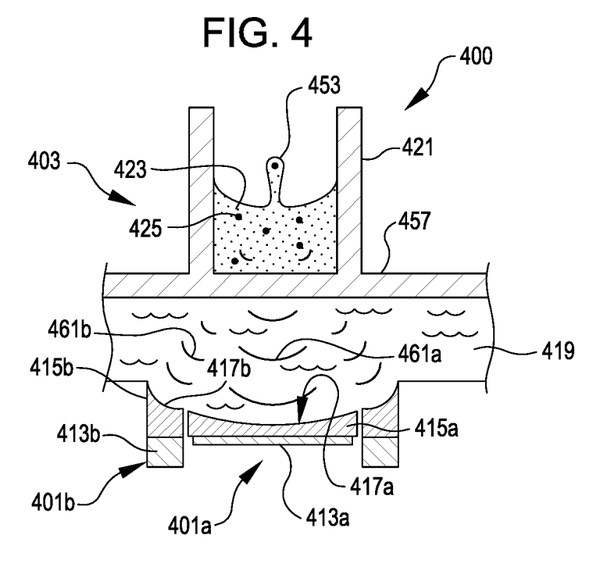
FIG. 4 is simplified schematic diagram of an embodiment of a focused acoustic radiation generator assembly that includes an annular ring focused acoustic radiation generation element for applying focused acoustic radiation to concentrate cells and/or particles near the upper surface of the fluid within the fluid sample reservoir and a disk shaped focused acoustic radiation generation element for applying focused acoustic radiation to eject a fluid sample from the fluid sample reservoir.

FIG. 4 is simplified schematic diagram of an assembly 400 in which a fluid sample reservoir 403 contains a fluid sample 423 with suspended particles 424. A reservoir body 421 of the fluid sample reservoir may extend away from a stage or plate 457 on which the fluid sample reservoir 403 rests or to which the fluid sample reservoir can be attached. Alternatively, the fluid sample reservoir 403 can be positioned without a sample stage or plate. The fluid sample reservoir 403 can be acoustically coupled with acoustic ejector assemblies 401a and 401b by way of an acoustic coupling medium 419. An outer, ring-focused acoustic ejector assembly 401b includes an annular acoustic radiation generator 413b, coupled with an annular and concave focusing element 415b having a curved face 417b, for applying focused acoustic radiation to concentrate cells and/or particles 425 within the fluid sample reservoir 403. Preferably, suspended particles 425 can be concentrated near an upper surface of the fluid sample 423 within the fluid sample reservoir 403. An inner, disk shaped ejector assembly 401a includes a disk-shaped focused acoustic radiation generator 413a coupled with a focusing element 415a, which can have a concave focusing surface 417 for applying focused radiation to eject a fluid sample from the fluid sample reservoir. In use, the outer, ring-focused acoustic ejector assembly 401b can generate a first tone burst of acoustic energy in the form of a first pattern of focused acoustic waves 461b at a pattern, frequency, and amplitude optimized to concentrate suspended particles 425 in the fluid sample 423 without ejecting droplets. Subsequently, the inner acoustic ejector assembly 401a can generate a second tone burst of focused acoustic energy in the form of a second pattern of focused acoustic waves 461a, typically at higher amplitudes, that is optimized to eject a droplet from the surface of the fluid sample 423, and from the same location at which particles 425 have been concentrated. The second tone burst can thus raise and detach particle-containing droplets 453 from the fluid sample 423.

FIG. 4 shows a configuration of the acoustic drive mechanism that combines acoustical generating devices for particle guiding (the transducer with the annular shape) and droplet ejection (the transducer element in the center). It should be noted that, for the purpose of optimizing the efficiency of the instrument, the design and operating frequencies of the guiding and drop generating transducers may need to be different. The geometry in the figure provides the flexibility of optimizing the center frequencies of the two generators to be different. It also enables independent beam-shape designs for the two generators. In many embodiments, the annular ring focused acoustic radiation generation element and the disk shaped focused acoustic radiation generation element have different thicknesses, indicative of the different frequencies of sound they generate, with the inside disk being thinner for droplets and the outer ring thicker for creating the desired particle motion such as mixing, de-agglomeration, trapping or concentration by nodal concentration field.

While it is understood that the geometry of FIG. 4 enables a greater flexibility with independent design of the particle guiding and drop ejecting transducers, it may be possible to combine them in a single transducer to provide acoustical drives for both functionalities.

EXAMPLE APPLICATIONS

Example 1: The devices shown in FIG. 1 can be implemented with control means (not shown) to enable rapid clean up and/or quality control of containers which may contain particulates. The signal generated by the electrodes spanning the measurement region and transmitted via the conductors to the analyzer can serve as the input to a decision-making means that can control the micro pump, acoustic radiation generator and positioning means for all the relevant components of the system including but not limited to aligning or swapping sample fluid containers/reservoirs, swapping or aligning (i.e., to focus it at the fluid surface) the acoustic radiation generator, or even changing the aperture assembly so the diameter of the measurement region is suitable for the particle sizes anticipated in the fluid in the sample containers.

The control means in this embodiment would prepare the fluid sample either by mixing or concentration of particles at the focal zone for droplet transfer. The control means would then instruct the micro pump to begin moving the fluid present at the outer electrode through the measurement zone. The signal generated is sent to the analyzer and then processed by the control means to determine how to change both the drop generation rate and micro pump flow rate to achieve a predetermined goal. For example, the process could continue until a predetermined number of droplets or total fluid volume was transferred and particle data recorded as part of a quality control procedure. Similarly, the control means could process the particle data and determine to stop the transfer or to continue based on many criteria such as the number of particles detected per unit time or volume, the number of particles in a given size range detected per unit time or volume and the like. Such a system configuration, when coupled with the ability to concentrate particles near the focal spot would enable the present invention to operate to efficiently extract particles from the container and to stop the transfer process once the data from the analyzer provided to the control means met the desired criteria.

As used in this specification and the appended claims, the singular forms "a," "an," and "the" include plural referents unless the context clearly dictates otherwise. Thus, for example, reference to "a reservoir" includes a single reservoir as well as a plurality of reservoirs, reference to "a fluid" includes a single fluid and a plurality of fluids, reference to "a frequency range" includes a single frequency range and a plurality of ranges, and reference to "an ejector" includes a single ejector as well as plurality of ejectors and the like.

It is to be understood that the invention is not limited to specific fluids, frequency ranges, or device structures, as such may vary. It is to be understood that while the invention has been described in conjunction with a number of specific embodiments, the foregoing description is intended to illustrate and not limit the scope of the invention. Other aspects, advantages and modifications will be apparent to those skilled in the art. All patents, patent applications, journal articles and other references cited herein are incorporated by reference in their entireties.

In the following, further examples are described to facilitate understanding of the invention:

Example A: A system for acoustic ejection of particle-containing droplets, comprising: an acoustic radiation generator;
a fluid sample reservoir containing a fluid sample, the fluid sample reservoir acoustically coupled with the acoustic radiation generator by an acoustic coupling medium; and
a controller comprising one or more processors and a memory device containing executable instructions that, when executed by the one or more processors, configure the controller to:
apply a first tone burst of focused acoustic radiation by the acoustic radiation generator to the fluid sample within the fluid sample reservoir to concentrate cells or particles within the fluid sample; and
apply a second tone burst of focused acoustic radiation by the acoustic radiation generator to the fluid sample at a target location corresponding to the concentrated cells or particles, to eject a droplet containing at least one cell or particle from the reservoir.

Example B: The system of any of the preceding examples, further comprising an analytical device having an inlet positioned in alignment with the acoustic radiation generator such that, when the droplet is ejected from the reservoir, the droplet contacts the inlet.

Example C: The system of example B, wherein the analytical device comprises an electrolytic particle counter configured to count or measure suspended particles by measuring electrical impedance of particle-containing fluid across an aperture.

Example D: The system of example B, wherein the analytical device comprises a visual particle counter configured to count or measure suspended particles by optically identifying the suspended particles.

Example E: The system of any of the preceding examples, further comprising a second fluid sample reservoir containing a second fluid sample, and an actuator configured to move the second fluid sample reservoir relative to the acoustic radiation generator, wherein the executable instructions, when executed by the one or more processors, further configure the controller to:

subsequent to the ejection of the droplet from the reservoir, cause the actuator to position the second fluid sample reservoir in alignment with the acoustic radiation generator;

apply a third tone burst of focused acoustic radiation by the acoustic radiation generator to the second fluid sample within the second sample reservoir to concentrate cells or particles within the second fluid sample; and apply a fourth tone burst of focused acoustic radiation by the acoustic radiation generator to the second sample fluid within the second sample reservoir at a target location corresponding to the concentrated cells or particles, to eject a second droplet containing at least one cell or particle from the second sample reservoir.

Example F: The system of any of the preceding examples, wherein the acoustic radiation generator comprises an annular element configured to focus the first tone burst to concentrate the cells or particles, and a disk-shaped element concentric within the annular element configured to focus the second tone burst to eject the droplet, wherein:

the first tone burst is applied via the annular element; and the second tone burst is applied via the disk-shaped element.

Example G: A method for acoustic transfer of particle-containing fluid droplets, the method comprising:

applying a first tone burst of focused acoustic radiation by an acoustic radiation generator to a fluid sample within a fluid sample reservoir containing suspended cells or particles such that the first tone burst concentrates the cells or particles at a target location within the fluid sample; and applying a second tone burst of focused acoustic radiation by the acoustic radiation generator to the fluid sample at the target location corresponding to the concentrated cells or particles to eject a droplet from the reservoir containing at least one cell or particle.

Example H: The method of any of the preceding examples, further comprising:

positioning the fluid sample reservoir in alignment with an inlet of an analytical device prior to applying the second tone burst; and ejecting the droplet from the fluid sample reservoir such that the droplet contacts the inlet of the analytical device.

Example I: The method of example H, wherein the analytical device comprises a particle counter having a detector configured to count cells or particles, the method further comprising:

performing a particle count on the droplet contacting the inlet of the analytical device.

Example J: The method of any of the preceding examples, wherein the first tone burst and the second tone burst are applied sequentially.

Example K: The method of any of the preceding examples, further comprising:

repeatedly applying the first tone burst to maintain an increased concentration of the cells or particles at the target location within the fluid sample.

Example L: The method of any of the preceding examples, wherein the first tone burst comprises one of a continuous waveform or a long tone burst configured to produce a standing acoustic wave in the fluid sample to trap the cells or particles in a resonant or anti-resonant node.

Example M: The method of any of the preceding examples, wherein the first tone burst comprises a swept frequency configured to push the cells or particles toward the target location within the fluid sample.

Example N: The method of any of the preceding examples, further comprising:

subsequent to the ejection of the droplet from the reservoir, position a second fluid sample reservoir containing a second fluid sample in alignment with the acoustic radiation generator;

apply a third tone burst of focused acoustic radiation by the acoustic radiation generator to the second fluid sample to concentrate cells or particles within the second fluid sample; and apply a fourth tone burst of focused acoustic radiation by the acoustic radiation generator to the second sample fluid within the second sample reservoir at a second target location corresponding to the concentrated cells or particles, to eject a second droplet from the second sample reservoir containing at least one cell or particle.

Example O: The method of any of the preceding examples, wherein:

the acoustic radiation generator comprises a first, annular acoustic radiation generator and a second, disk-shaped acoustic radiation generator positioned concentric with the first acoustic radiation generator;

the first tone burst is generated by the first acoustic radiation generator; and the second tone burst is generated by the second acoustic radiation generator.

Example P: The method of any of the preceding examples, further comprising:

adjusting a vertical position of the fluid sample reservoir to align a focal region of the first tone burst or the second tone burst with an upper surface of the fluid sample.

Example Q: A system, comprising:
an acoustic radiation generator;
a fluid sample reservoir containing a fluid sample, the fluid sample reservoir acoustically coupled with the acoustic radiation generator by an acoustic coupling medium;
an analytical instrument comprising an inlet configured to receive fluid droplets; and
a controller comprising one or more processors and a memory device containing executable instructions that, when executed by the one or more processors, configure the controller to:
apply a first tone burst of focused acoustic radiation by the acoustic radiation generator to the fluid sample within the fluid sample reservoir to concentrate cells or particles within the fluid sample; and
apply a second tone burst of focused acoustic radiation by the acoustic radiation generator to the fluid sample at a target location corresponding to the concentrated cells or particles, to eject a droplet containing at least one cell or particle from the reservoir to the inlet of the analytical instrument.

Example R: The system of any of the preceding examples, wherein:
the analytical instrument comprises a particle counter having a detector configured to count cells or particles; and
the executable instructions, when executed by the one or more processors, further configure the controller to:
cause the analytical instrument to perform a particle count on a transferred fluid sample that includes the ejected droplet after ejection of the droplet from the fluid sample reservoir to the inlet.

Example S: The system of any of the preceding examples, wherein:
the analytical instrument comprises a pump fluidly connected with the inlet of the analytical device; and
the executable instructions, when executed by the one or more processors, further configure the controller to:
detect, via the detector, whether an ejected droplet is present at the inlet; and
in response to detecting the ejected droplet, cause the pump to pull fluid through the inlet;

Example T: The system of any of the preceding examples, wherein the inlet of the analytical instrument comprises a non-wetting material that resists retention of residue at the inlet.

Example U: A method for acoustic transfer of particle-containing fluid droplets, the method comprising:
positioning a fluid sample reservoir containing a fluid sample having suspended cells or particles that is acoustically coupled with an acoustic radiation generator in alignment with an inlet of an analytical device configured for counting cells or particles; and
applying an ejection tone burst of focused acoustic radiation by the acoustic radiation generator to the fluid sample within the fluid sample reservoir to eject a droplet from the fluid sample reservoir such that the droplet contacts the inlet of the analytical device, the droplet containing at least one cell or particle.

Example V: The method of example U, further comprising:
concentrating the cells or particles at a target location within the fluid sample prior to applying the ejection tone burst by applying a concentrating tone burst of focused acoustic radiation by the acoustic radiation generator to the fluid sample, the concentrating tone burst configured to move the cells or particles toward the target location within the fluid sample without causing droplet ejection.

Example W. The method of any of the preceding examples, wherein the concentrating tone burst and the ejection tone burst are applied sequentially.

Example X. The method of any of the preceding examples, further comprising:
repeatedly applying the concentrating tone burst to maintain an increased concentration of the cells or particles at the target location within the fluid sample.

Example Y. The method of any of the preceding examples, wherein the concentrating tone burst comprises one of a continuous waveform or a long tone burst configured to produce a standing acoustic wave in the fluid sample to trap the cells or particles in a resonant or anti-resonant node.

Example Z. The method of any of the preceding examples, wherein the concentrating tone burst comprises a swept frequency configured to push the cells or particles toward the target location within the fluid sample.

Example AA. The method of any of the preceding examples, wherein:
the acoustic radiation generator comprises an annular first acoustic radiation generator and a disk-shaped second acoustic radiation generator positioned concentric with the first acoustic radiation generator;
the concentrating tone burst is generated by the first acoustic radiation generator; and
the ejection tone burst is generated by the second acoustic radiation generator.

Example AB. The method of any of the preceding examples, further comprising:
subsequent to the ejection of the droplet from the fluid sample reservoir, position a second fluid sample reservoir containing a second fluid sample in alignment with the acoustic radiation generator;
apply a second concentrating tone burst of focused acoustic radiation by the acoustic radiation generator to the second fluid sample to concentrate cells or particles within the second fluid sample; and
apply a second ejection tone burst of focused acoustic radiation by the acoustic radiation generator to the second sample fluid within the second fluid sample reservoir at a second target location corresponding to the concentrated cells or particles, to eject a second droplet from the second fluid sample reservoir containing at least one cell or particle.

Example AC. The method of any of the preceding examples, further comprising:
adjusting a vertical position of the fluid sample reservoir to align a focal region of the ejection tone burst with an upper surface of the fluid sample.

Example AD. The method of any of the preceding examples, further comprising:
performing a particle count by the analytical device on the droplet contacting the inlet of the analytical device.

Example AE. The method of example AD, wherein:
the analytical device comprises an electrolytic particle counter configured to count or measure suspended particles by measuring electrical impedance of cell- or particle-containing fluid across an aperture of the analytical device fluidly coupled with the inlet; and
performing the particle count comprises electrically sensing passage of the cells or particles through the aperture from the droplet contacting the inlet.

Example AF. The method of example AE, further comprising:

ejecting additional subsequent droplets from the fluid sample contained in the fluid sample reservoir to supplement the droplet contacting the inlet of the analytical device; and cease ejecting the additional subsequent droplets from the fluid sample based on an attribute of the particle count.

Example AG. The method of example AF, wherein the attribute of the particle count is one of a number of cells or particles, a size of cells or particles, a number of cells or particles per unit time, a number of cells or particles within a predetermined range of size, or a total volume passed through the analytical device.

Example AH. A system for acoustic ejection of particle-containing droplets, comprising:
an acoustic radiation generator;
a fluid sample reservoir containing a fluid sample, the fluid sample reservoir acoustically coupled with the acoustic radiation generator by an acoustic coupling medium;
an analytical device configured for counting cells or particles, the analytical device comprising an inlet positioned in alignment with at least one of the acoustic radiation generator and fluid sample reservoir; and
a controller comprising one or more processors and a memory device containing executable instructions that, when executed by the one or more processors, configure the controller to:
apply an ejection tone burst of focused acoustic radiation by the acoustic radiation generator to the fluid sample at a target location to eject a droplet containing at least one cell or particle from the fluid sample reservoir such that the droplet contacts the inlet of the analytical device.

Example AI. The system of example AH, wherein the executable instructions, when executed by the one or more processors, further configure the controller to:
concentrate the cells or particles at the target location within the fluid sample prior to applying the ejection tone burst by applying a concentrating tone burst of focused acoustic radiation by the acoustic radiation generator to the fluid sample within the fluid sample reservoir to concentrate cells or particles within the fluid sample at the target location without causing droplet ejection.

Example AJ. The system of any of the preceding examples, wherein the acoustic radiation generator comprises an annular element configured to focus the concentrating tone burst to concentrate the cells or particles, and a disk-shaped element concentric within the annular element configured to focus the ejection tone burst to eject the droplet, wherein:
the concentrating tone burst is applied via the annular element; and
the ejection tone burst is applied via the disk-shaped element.

Example AK. The system of any of the preceding claims, wherein the executable instructions, when executed by the one or more processors, further configure the controller to:
apply subsequent additional ejection tone bursts to eject additional subsequent droplets from the fluid sample contained in the fluid sample reservoir to supplement the droplet contacting the inlet of the analytical device;
cause the analytical device to obtain a particle count of cells or particles contained in the droplet contacting the inlet of the analytical device; and
cease ejecting the additional subsequent droplets based on an attribute of the particle count.

Example AL. The system of example AK, wherein the attribute of the particle count is one of a number of cells or particles, a size of cells or particles, a number of cells or particles per unit time, a number of cells or particles within a predetermined range of size, or a total volume passed through the analytical device.

Example AM. The system of any of the preceding examples, further comprising a second fluid sample reservoir containing a second fluid sample, and an actuator configured to move the second fluid sample reservoir relative to the acoustic radiation generator, wherein the executable instructions, when executed by the one or more processors, further configure the controller to:
subsequent to the ejection of the droplet from the fluid sample reservoir, cause the actuator to position the second fluid sample reservoir in alignment with the acoustic radiation generator; and
apply a second ejection tone burst of focused acoustic radiation by the acoustic radiation generator to the second sample fluid within the second fluid sample reservoir to eject a second droplet containing from the second fluid sample reservoir such that the second droplet contacts the inlet of the analytical device.

Example AN. The system of any of the preceding examples, wherein:
the second fluid sample comprises additional cells or particles; and
the executable instructions, when executed by the one or more processors, further configure the controller to:
concentrate the additional cells or particles by applying a second concentrating tone burst of focused acoustic radiation by the acoustic radiation generator to the second fluid sample within the second fluid sample reservoir.

Example AO. The system of any of the preceding examples, wherein the analytical device comprises one of an electrolytic particle counter configured to count or measure suspended cells or particles by measuring electrical impedance of particle-containing fluid across an aperture fluidly coupled with the inlet or a visual particle counter configured to count or measure suspended cells or particles by optically identifying the at least one cell or particle contained in the ejected droplet contacting the inlet.

What is claimed is:

1. A method for acoustic transfer of particle-containing fluid droplets, the method comprising:
    positioning a fluid sample reservoir containing a fluid sample having suspended cells or particles that is acoustically coupled with an acoustic radiation generator in alignment with an inlet of an analytical device;
    applying an ejection tone burst of focused acoustic radiation by the acoustic radiation generator to the fluid sample within the fluid sample reservoir to eject a droplet from the fluid sample reservoir such that the droplet contacts the inlet of the analytical device, the droplet containing at least one cell or particle; and
    concentrating the suspended cells or particles at a target location within the fluid sample prior to applying the ejection tone burst by applying a concentrating tone burst of focused acoustic radiation by the acoustic radiation generator to the fluid sample, the concentrating tone burst configured to move the suspended cells or particles toward the target location within the fluid sample without causing droplet ejection.

2. The method of claim 1, wherein the concentrating tone burst and the ejection tone burst are applied sequentially.

3. The method of claim 1, further comprising: repeatedly applying the concentrating tone burst to maintain an increased concentration of the cells or particles at the target location within the fluid sample.

4. The method of claim 1, wherein the concentrating tone burst comprises one of a continuous waveform or a long tone burst configured to produce a standing acoustic wave in the fluid sample to trap the cells or particles in a resonant or anti-resonant node.

5. The method of claim 1, wherein the concentrating tone burst comprises a swept frequency configured to push the cells or particles toward the target location within the fluid sample.

6. The method of claim 1, wherein: the acoustic radiation generator comprises an annular first acoustic radiation generator and a disk-shaped second acoustic radiation generator positioned concentric with the first acoustic radiation generator; the concentrating tone burst is generated by the first acoustic radiation generator; and the ejection tone burst is generated by the second acoustic radiation generator.

7. The method of claim 1, further comprising: subsequent to the ejection of the droplet from the fluid sample reservoir, positioning a second fluid sample reservoir containing a second fluid sample in alignment with the acoustic radiation generator; applying a second concentrating tone burst of focused acoustic radiation by the acoustic radiation generator to the second fluid sample to concentrate cells or particles within the second fluid sample; and applying a second ejection tone burst of focused acoustic radiation by the acoustic radiation generator to the second sample fluid within the second fluid sample reservoir at a second target location corresponding to the concentrated cells or particles, to ejecta second droplet from the second fluid sample reservoir containing at least one cell or particle.

8. The method of claim 1, further comprising:
adjusting a vertical position of the fluid sample reservoir to align a focal region of the ejection tone burst with an upper surface of the fluid sample.

9. The method of claim 1, further comprising:
performing a particle count by the analytical device on the droplet contacting the inlet of the analytical device.

10. The method of claim 9, wherein:
the analytical device comprises an electrolytic particle counter configured to count or measure the suspended cells or particles in the droplet contacting the inlet of the analytical device by measuring electrical impedance of fluid drawn from the droplet across an aperture of the analytical device fluidly coupled with the inlet; and
performing the particle count comprises electrically sensing passage of the suspended cells or particles through the aperture from the droplet contacting the inlet.

11. The method of claim 9, further comprising:
ejecting additional subsequent droplets from the fluid sample contained in the fluid sample reservoir to supplement the droplet contacting the inlet of the analytical device; and
ceasing ejecting the additional subsequent droplets from the fluid sample based on an attribute of the particle count.

12. The method of claim 11, wherein the attribute of the particle count is one of a number of cells or particles, a size of cells or particles, a number of cells or particles per unit time, a number of cells or particles within a predetermined range of size, or a total volume passed through the analytical device.

13. The method of claim 11, wherein the analytical device is configured for counting cells or particle.

* * * * *